US006878685B2

(12) United States Patent
Soll et al.

(10) Patent No.: US 6,878,685 B2
(45) Date of Patent: Apr. 12, 2005

(54) HIV-ENCODED CHEMOATTRACTANT

(75) Inventors: David R. Soll, Iowa City, IA (US); Damon Shutt, Iowa City, IA (US)

(73) Assignee: University of Iowa Research Foundation, Iowa City, IA (US)

(*) Notice: Subject to any disclaimer, the term of this patent is extended or adjusted under 35 U.S.C. 154(b) by 0 days.

(21) Appl. No.: 10/274,361

(22) Filed: Oct. 21, 2002

(65) Prior Publication Data

US 2004/0076643 A1 Apr. 22, 2004

Related U.S. Application Data

(63) Continuation of application No. 09/479,596, filed on Jan. 7, 2000, now abandoned.
(60) Provisional application No. 60/116,929, filed on Jan. 22, 1999.

(51) Int. Cl.$^7$ .................. A61K 38/01; A61K 38/16; A61K 38/19; A61K 51/00; A61K 51/08; A61K 45/08; A61K 39/21

(52) U.S. Cl. .................. 514/2; 514/12; 530/350; 530/300; 530/205.1; 530/208.1; 530/85.1

(58) Field of Search .................. 424/93.2, 205.1, 424/208.1, 85.2; 530/350, 300

(56) References Cited

U.S. PATENT DOCUMENTS

| 5,159,002 A | * 10/1992 | Pandey .................. 549/271 |
|---|---|---|
| 5,320,094 A | 6/1994 | Laube et al. ........... 128/203.12 |
| 5,428,023 A | 6/1995 | Russell-Jones et al. ....... 514/21 |
| 5,574,018 A | 11/1996 | Habberfield et al. .......... 514/21 |
| 5,606,026 A | 2/1997 | Rodman .................. 530/387.9 |
| 5,747,526 A | 5/1998 | Hollinshead ................ 514/488 |
| 5,891,994 A | * 4/1999 | Goldstein .................. 530/329 |
| 5,968,514 A | * 10/1999 | Johnson et al. .......... 424/188.1 |

FOREIGN PATENT DOCUMENTS

WO          93/25221         12/1993

OTHER PUBLICATIONS

Joseph et al. FEBE Letters 2003, vol. 548, pp. 37–42.*
Kestler et al. Cell 1991, vol. 65, No. 4, pp. 651–662.*
Popik et al. J. Virol. 1994, vol. 68, No. 3, pp. 1324–1333.*
Skelton et al. Biochemistry 1995, vol. 34, pp. 5329–5324.*
Ylisastigue et al. AIDS 1998, vol. 12, pp. 977–984.*
Shepard et al. Nature 1981, vol. 294, pp. 563–565.*
Hinkula et al. J. Virol. 1997, vol. 71, pp. 5528–5539.*
Kedzierska et al. AIDS 2001, vol. 15, pp. 945–955.*
Petit et al. Virol. 2001, vol. 286, pp. 225–236.*
Chun et al.; Induction of HIV–1 replication . . . ; J. Exp. Med.; vol. 188, No. 1; pp. 83–91, Jul. 1998.*
Gait et al.; Progress in anti–HIV structure–based drug design; TIBTECH; vol. 13; pp. 430–438, Oct. 1995.*

R. Lafrenie et al., "HIV 1 Tat protein promotes chemotaxis and invasive behaviour by monocytes", J. Immunol. vol. 157, 1996 pp. 974–977, XP000929467.
A. Albini et al., "HIV–1 Tat protein mimicry of chemokines", Proc. Natl. Acad. Sci. USA, vol. 95, 1998 pp. 13153–13158, XP002146039.
D. Shutt et al., "HIV–induced T cell syncytia release a two–component T helper cell chemoattractant composed Of Nef and Tat", J. Cell Sci., vol. 112, 1999 pp. 3931–3941, XP000938498.
Benichou et al.; "Physical Interaction of the HIV–1 Nef Protein with β–COP, a Component of Non–clathrin–coated Vesicles Essential for Membrane Traffic"; The Journal of Biological Chemistry; vol. 269, No. 48; Dec. 2, 1994; pp. 30073–30076.
Beger et al.; "Reconsidering Targeted Toxins to Eliminate HIV Infection: You Gotta Have HAART"; Proc. Natl. Acad. Sci. USA; vol. 95; Sep. 1998; pp. 11511–11513.
Boyden; "The Chemotactic Effect of Mixtures of Antibody and Antigen on Polymorphoneclear Leucocytes"; Aug. 1961; pp. 453–466.
Center et al.; "Interleukin 16 and Its Function as a CD4 Ligand"; Immunology Today; vol. 17, No. 10; Oct. 1996; pp. 466–481.
Chen et al.; Intracellular Antibodies as a New Class of Therapeutic Molecules for Gene Therapy; Human Gene Therapy; vol. 5,; 1994; pp. 595–601.
Teixeira et al.; "Cytokine Profile Associated to Effector Functions of Human T Cell Clones Specific for *Schistosoma mansoni* Antigens"; Human Immunology; vol. 59; 1998; pp. 219–224.
Chun et al.; "Induction of HIV–1 Replication in Latently Infected CD4$^+$ T Cells Using a Combination of Cytokines"; The Journal of Experimental Medicine; vol. 188, No. 1; Jul. 6, 1998; pp. 83–91.

(Continued)

Primary Examiner—James Housel
Assistant Examiner—Bao Qun Li
(74) Attorney, Agent, or Firm—Foley & Lardner LLP (57) ABSTRACT

The combination of HIV proteins Tat and Nef is chemotactic for CD4+ cells. Utilizing the capacity of Tat and Nef to modulate CD4+ cell trafficking and infiltration, the invention provides various treatment modes for individuals infected with HIV. The invention further provides treatment modes for other localized diseases by controlling CD4+ cell trafficking and infiltration. In particular, the invention provides methodology for promoting CD4+ cell chemotaxis to a localized site of infection as a means of augmenting the efficacy of extant chemotherapeutic methods. The invention further provides methodology for diverting CD4+ cell infiltration from a localized site where the presence of CD4+ cells is detrimental to the clinical outcome, by providing a composition comprising Tat and Nef at a distinct site, such as blood, within the individual where the accumulation of CD4+ cells is less detrimental.

7 Claims, 4 Drawing Sheets

OTHER PUBLICATIONS

Clerici et al.; "A $T_H 1 \rightarrow T_H 2$ Switch is A Critical Step in the Etiology of HIV Infection"; Immunology Today; vol. 14, No. 3; 1993; pp. 107–111.

Desmedt et al.; "Macrophages Induce Cellular Immunity by Activating Th1 Cell Responses and Suppressing Th2 Cell Responses[1]"; The Journal of Immunology; 1998; pp. 5300–5308.

Frankel et al.; "Replication of HIV–1 in Dendritic Cell– Derived Syncytia at the Mucosal Surface of the Adenoid"; Science; vol. 272; Apr. 5, 1996; pp. 115–117.

Gratton et al.; "Molecular Analysis of the Cytoplasmic Domain of Cd4"; The Journal of Immunology; 1996; pp. 3305–3311.

Huffnagle et al.; "The Role of Monocyte Chemotactic Protein–1 (MCP-1) in the Recruitment of Monocytes and $CD4^+$ T Cells During a Pulmonary *Cryptococcus neoformans* Infection[1]"; The Journal of Immunology; 1995; pp. 4790–4797.

Kowalski et al.; "functional Regions of the Envelope glycoprotein of Human Immunodeficiency Virus Type 1"; Reports; Sep. 11, 1987; pp. 1351–1355.

Levy; "Pathogenesis of Human Immunodeficiency Virus Infection"; Microbiological Reviews; vol. 57, No. 1; Mar. 1993; pp. 183–289.

Lifson et al.; Induction of CD4–dependent Cell Fusion by the HTLV–III LAV Envelope Glycoprotein; Letters to Nature; vol. 323; Oct. 23, 1986; pp. 725–728.

Lifson et al.; "AIDS Retrovirus Induced Cytopathology; Giant Cell formation and Involvement of CD4 Antigen"; Reports; May 30, 1986; pp. 1123–1127.

McCutcheon; "Chemotaxis in Leukocytes"; Physiological Reviews; vol. 26, No. 3; Jul. 1946; pp. 319–336.

McDougal et al.; "Binding of HTLV–III/LAV to $T4^+$ T Cells by a Complex of the 110K Viral Protein and the T4 Molecule"; Science; vol. 231; Jan. 24, 1986; pp. 382–385.

Smith et al.; "Monoclonal Antibody and Enzymatic Profiles of Human Malignant T–Lymphoid Cells and Derived Cell Lines[1]"; Cancer Research; vol. 44; Dec. 1984; pp. 5657–5660.

Miedema; "Immunological Abnormalities in the Natural History of HIV Infection: Mechanisms and Clinical Relevance"; Immunodeficiency Reviews; vol. 3; 1992; pp. 173–193.

Murphy et al.; "Human RANTES Induces the Migration of Human T Lymphocetes into the Peripheral Tissues of Mice with Severe Combined Immune Deficiency"; Eur. Journal of Immunology; vol. 24; 1994; pp. 1823–1827.

Otake et al.; "The Carboxyl–Terminal Region of HIV–1 Nef Protein is a Cell Surface Domain that can Interact with $CD4^+$ T Cells"; The Journal of Immunology; 1994; pp. 5826–5837.

Proost et al.; "The Role of Chemokines in Inflammation"; Review; vol. 26; 1996; pp. 211–223.

Rhodes; "Measurement of Chemotaxis in Boyden Chamber Filter Assays, is the Checkerboard Correction Valid?"; Journal of Immunology Methods; vol. 49; 1982; pp. 235–236.

Richman et al.; "The Impact of the Syncytium–Inducing Phenotype of Human Immunodeficiency Virus on Disease Progression"; The Journal of Infectious Diseases; vol. 169; 1994; pp. 968–974.

Ryan et al.; "The CD4–associated Tyrosine Kinase $p56^{lck}$ Is Required for Lymphocyte Chemoattractant Factor–induced T Lymphocyte Migration"; The Journal of Biological Chemistry; vol. 270, No. 29; Jul. 21, 1995; pp. 17081–17086.

Maniatis et al.; "Molecular Cloning"; A Laboratory Manual; 1982; 2 Sheets.

Schneider et al.; "Shedding and Interspecies Type Sero–reactivity of the Envelope Glycopolypeptide gp120 of the Human Immunodeficiency Virus"; J. Gen. Virol.; vol. 67; 1986; pp. 2533–2538.

Coffman; "Regulation of Immunity to Parasites by T Cells and T Cell–Derived Cytokines[1]"; Annu. Rec. Immunology; vol. 10; 1992; pp. 385–409.

Shutt et al.; "HIV–Induced Syncytia in Peripheral Blood Cell Cultures Crawl by Extending Giant Pseudopods"; Cellular Immunology; vol. 166; 1995; pp. 261–274.

Shutt et al.; "T Cell Syncytia Induced by HIV Release"; Journal of Cell Science; vol. 111, No. 1; Jan. 1998; pp. 99–109.

Soll; "The Use of Computers in Understanding How Animal Cells Crawl"; International Review of Cytology; vol. 163; 1995; pp. 43–104.

Standiford; "Cytokines and Pulmonary Host Defenses"; Journal of Infectious Diseases; vol. 3; 1997; pp. 81–88.

Sylwester et al.; "HIV–Induced Syncytia of a T Cell Line Form Single Giant Pseudopods and Are Motile"; Journal of Cell Science; vol. 106; 1996; pp. 941–953.

Murphy et al.; "Phagocytosis of Individual $CD4^+$ T Cells by HIV–Induced T Cell Syncytia"; Aids Research and Human Retroviruses; vol. 11, No. 4; 1995; pp. 433–442.

Thestrup–Pedersen et al.; "T Lymphocyte Chemotaxis and Skin Diseases"; Experimental Dermatology; vol. 4; 1995; pp. 281–290.

Harada et al.; Infection of HTLV–III/LAV in HTLV–1 Carrying Cells MT–2 and MT–4 and Application in a Plaque Assay; Science; vol. 229; 1985; pp. 563–566.

Sylwester et al.; "HIV–Induced T Cell Syncytia Are Self–Pernetuating and the Primary Cause of T Cell Death in Culture[1]"; The Journal of Immunology; 1997; pp. 3996–4007.

Sylwester et al.; "The Invasive and Destructive Behavior of HIV–Induced T Cell Syncytia on Collagen and Endothelium"; Journal of Leukocyte Biology; vol. 63, No. 2; Feb. 1998; pp. 233–244.

Taub et al.; "Manocyte Chemotactic Protein–1 (MCP–1), –2, and –3 Are Chemotactic for Human T Lymphocytes"; The Journal of Clinical Investigation; vol. 95; Mar. 1995; pp. 1370–1376.

Taub et al.; "The Voodoo That They Do So Well"; Cytokine &Growth Factor Reviews; vol. 7, No. 4; 1996; pp. 355–376.

Van Deventer et al.; "Immunomodulatory Antibodies"; Review; Aug. 1996; pp. 55–59.

Wessels et al.; "cAMP–Mediated Inhibition of Intracellular Particle Movement and Actin Reorganization in Dictyostelium"; The Journal of Cell Biology; vol. 109, No. 6; Dec. 1989; pp. 2841–2851.

Wilkinson; "Micropore Filter Methods for Leukocyte Chemotaxis", Methods in Enzymology; vol. 162; 1962; pp. 38–50.

Zigmond et al.; "Leukocyte Locomotion and Chemotaxis"; The Journal of experimental Medicine; vol. 137; 1973; pp. 387–410.

Zigmond; "A New Visual Assay of Leukicyte Chemotaxis"; 1978; pp. 57–66.

Van De Kerkhof et al. "Transtition From Symptomless To Lesional Psoriatic Skin"; Clinical and Experimental Dermatology; vol. 21; 1996; pp. 325–329.

Gelderblom et al.; "Loss of Envelope Antigens of HTLV–III/LAV, A Factor in Aids Pathogenesis?"; The Lancet; Nov. 2, 1995; pp. 1016–1017.

Jones et al.; "Oral Delivery Systems for Microparticles"; Abstract Patent EP0531497.

* cited by examiner

HIV-ENCODED CHEMOATTRACTANT

This application is a continuation of U.S. application Ser. No. 09/479,596, filed Jan. 7, 2000 now abandoned which claims priority to U.S. Provisional Application Ser. No. 60/116,929 filed on Jan. 22, 1999.

BACKGROUND OF THE INVENTION

The recruitment and trafficking of CD4+ cells in the body is modulated by chemoattractant proteins, typically produced in response to inflammatory stimuli. Reviewed in Taub (1996). Directed CD4+ cell movement up concentration gradients of chemoattractants results in trafficking of CD4+ cells out of the circulation, through the vascular endothelium, and into peripheral tissue to the site of highest localized concentration of chemoattractants. By secreting their own chemoattractants, CD4+ cells may direct the subsequent accumulation of various other cells types involved in host defense mechanisms, such as neutrophils. While the localized accumulation of CD4+ cells may be important for defense against infection, accumulation of CD4+ cells can also be part of a chain of events resulting in an unwanted inflammatory response.

For example, infiltration and accumulation of CD4+ cells in the respiratory tract helps mediate clearance of *Cryptococcus neoformans* infections, which otherwise will disseminate to cause meningitis. Huffnagle et al. (1995). By contrast, uncontrolled infiltration and activation of CD4+ cells in response to bacterial antigens appears to be the underlying cause of inflammatory bowel disease. Van Deventer et al. (1997). Localized CD4+ cell accumulation has been implicated specifically in response to infections and inflammatory conditions, including inflammatory bowl disease, bacterial infection, viral infection, atherosclerosis, asthma, graft versus host disease (GVHD), endotoxemia, uveoretinitis, psoriasis, and granulomatous diseases. Center (1996); Jinquan et al. (1995); Taub (1996); Van de Kerkhof et al. (1996). See, in general, Staniford (1997).

Another disease associated with CD4+ cell physiology is HIV infection. A defining feature of progression of HIV infection to Acquired Immune Deficiency Syndrome (AIDS) is a decline in the number of CD4+ cells in the infected individual. Reviewed in Levy (1993). Disease progression also strongly correlates with a switch from non-syncytium-forming (NSI) HIV variants to syncytium-forming (SI) variants within infected individuals. Richman et al. (1994); Miedema (1992). For example, a recent study found that the adenoid tissue of 13 of 13 asymptomatic individuals contained syncytia formed apparently from fusion of dendritic cells and T cells. Frankel et al. (1996).

Recent studies have provided a potential link between CD4+ cell loss and syncytium formation by implicating CD4+ cell chemotaxis in the propagation of syncytia. Syncytia have been found to release CD4+ cell chemoattractants, potentially providing a mechanism by which CD4+ cells can be recruited throughout the body to their demise by incorporation into short-lived syncytia. Shutt et al. (1998).

Syncytia are multinucleated conglomerates of HIV-infected cells having up to many thousands of times the volume of a single cell. They are formed when the virally encoded glycoprotein gp120 on the surface of infected cells interacts with the CD4 receptor of uninfected cells to initiate cell fusion. Kowolski et al. (1987); McDougal et al. (1986); Lifson et al. (1986a,b). Syncytia also are phagocytotic and may engulf entire CD4+ cells. Sylwester et al. (1995). In vitro studies have indicated that up to 90% of T cell death is accounted for by their incorporation into syncytia. Vast quantities of HIV are released upon the death of syncytia, which infect non-fused CD4+ cells, thus creating a self-perpetuating cycle of infection and CD4+ cell death. Sylwester et al. (1997).

In addition to perpetuating HIV infection, syncytia can directly cause tissue destruction by virtue of motile properties retained from constituent lymphocyte cells. Soll, 1997. Syncytia move by extending and retracting giant pseudopodia and filopodia, which penetrate and disrupt collagen and endothelial tissue substrates. Sylwester et al. (1998). The ability of syncytia to degrade and extravasate through endothelial tissue may be related to the destruction of lymph node architecture and the leakiness of blood vessels in an individual bearing the syncytium-inducing variant of HIV. This property may also account for the apparent absence of syncytia in blood vessels, since these large cells would likely become stuck in capillaries, where they could then extravasate into the periphery.

In video recordings of fields of single cells and syncytia in the act of fusing in vitro, it was apparent that single cells and small syncytia moved in a persistent and directed fashion towards large syncytia, suggesting that the latter released a T cell chemoattractant. To confirm this hypothesis, a specialized single-cell chemotaxis chamber was used to discriminate chemokinesis from chemotaxis. Shutt et al. (1998). Chemokinesis is accelerated, non-vectorial movement, while chemotaxis is directed movement of cells up a concentration gradient of a chemoattractant. The microfilter assay, first introduced by Boyden (1962), was not used because it cannot unambiguously distinguish chemotaxis form chemokinesis, even when the appropriate corrections are performed. Wilkinson (1988); Zigmond (1978); Zigmond et al. (1973); Rhodes (1982); Shutt et al. (1998).

Syncytia release two chemotactic components into the supernatant, having approximate molecular weights of 30 and 120 kDa. Shutt et al. (1998). Virally encoded glycoprotein gp120 is released into the medium by HIV-infected cells, implicating the 120 kDa chemoattractant as gp120. Gelderblom et al. (1985); Schneider et al. (1986). This was confirmed by the ability of anti-gp120 antibody to block the high molecular weight chemoattractant, and by the ability of purified gp120 to attract T cells. Shutt et al. (1998).

The identity of the lower molecular weight component remained unknown. HIV virus encodes several low molecular weight proteins, including Rev, p24, Nef (27 kDa), a negative regulator of viral replication, and Tat (15.5 kDa), an activator of viral gene expression, but there was no suggestion in the art that these proteins function as chemoattractants, with the possible exception of Tat. Tat induces the migration of monocyte-derived dendritic cells and monocytes across a membrane in a Boyden chamber in a concentration-dependent manner. Benelli et al. (1998). While these authors concluded that Tat acted as a dendritic cell chemoattractant, the absence of critical controls suggested by Zigmond et al. (1973) for the microfilter assay complicates the distinction between a chemotactic and a chemokinetic effect.

There have been, however, no reports of either chemotactic or chemokinetic activity by the other low molecular weight HIV proteins. Although interactions of Nef with various cellular proteins have been characterized, the known interactions are not suggestive of chemotactic or chemokinetic activity. The activity of a putative CD4+ cell chemoattractant, interleukin-16, is thought to require coupling between CD4 and the cellular kinase p56$^{lck}$. Ryan et al. (1995). However, intracellular Nef expression has been demonstrated to reduce cell surface expression of CD4. Gratton et al. (1996). Further, Nef apparently disrupts the interaction between CD4 and p56$^{lck}$, either directly or, more likely, indirectly through other proteins recruited by Nef. Otake et al. (1994); Benichou et al. (1994).

Thus, there is a need in the art to modulate CD4+ cell chemotaxis. Such a capability will enhance treatment of a disease associated with localized CD4+ cell accumulation. It is desirable to direct CD4+ chemotaxis to a localized site of infection in circumstances where CD4+ cell intervention is desired for a favorable clinical outcome. Likewise, it is desirable to prevent CD4+ cell chemotaxis at sites where this accumulation leads to undesired inflammatory reactions. Alternately, it is desirable to redirect CD4+ cell accumulation to sites where their accumulation will be less detrimental.

Modulation of CD4+ cell chemotaxis would be desirable in treatment of HIV infection as a means of inhibiting the syncytium-induced chemotaxis of CD4+ cells out of circulation and into peripheral or lymphoid tissue, where they may fuse with or be engulfed and destroyed by syncytia. By inhibiting syncytium-mediated T cell death, the progression of HIV infection into AIDS may be retarded.

SUMMARY OF THE INVENTION

The invention provides a method for modulating CD4+ cell chemotaxis. This is accomplished by a composition comprising a combination of the HIV proteins Tat and Nef. By themselves, these proteins have a chemokinetic effect on CD4+ cells. Surprisingly, in combination, they are chemotactic for CD4+ cells. Thus, the chemoattractant activity of the apparent 30 kDa molecular weight syncytium-conditioned medium component is actually due to the combined effects of Nef and Tat.

CD4+ cell chemotaxis may be stimulated by administering a composition comprising Tat and Nef. This composition may be locally administered to a site of infection to promote CD4+ cell chemotaxis where the presence of CD4+ cells is desirable to the clinical outcome. Alternately, peripheral administration of the composition may be used to divert CD4+ cell accumulation from sites where their presence is detrimental. Preferably, the composition may be administered along with a chemotherapeutic agent. In this embodiment, the local infiltration of CD4+ cells stimulated by Tat and Nef augments the therapeutic value of the chemotherapeutic agent.

In a preferred embodiment, the composition is useful for the treatment of HIV infection. Extravasation of CD4+ cells into peripheral tissue may be inhibited by systemically administering the inventive composition. High systemic concentrations of Tat and Nef may mask or obscure gradients of these same molecules originating from syncytia in peripheral tissue. Because chemotaxis is directed toward higher concentrations of the chemoattractant, systemic administration of Tat and Nef would inhibit the migration of CD4+ cells into the periphery and would consequently inhibit their recruitment into syncytia.

Accordingly, it is an object of the invention to provide a pharmacological composition comprising Tat and Nef proteins, or a functional fragment or derivative thereof, in an amount effective to induce CD4+ cell chemotaxis. In a preferred embodiment, Tat and Nef are administered as purified proteins in a pharmacologically acceptable diluent, carrier, stabilizer, or excipient. In a more preferred embodiment, Tat and Nef are administered in the presence of an additional chemotherapeutic agent, which is delivered in an effective amount to treat the infection. In another preferred embodiment, Tat and Nef are produced recombinantly.

The invention also provides a method of treating a disease, comprising administering a composition comprising Tat and Nef to promote CD4+ cell chemotaxis and accumulation at the site of administration, where the accumulation of CD4+ cells is desirable to the therapeutic outcome of a disease. In a preferred embodiment, the site of administration is at a localized focus of infection, and a chemotherapeutic agent is co-administered with Tat and Nef, so that the infiltration of CD4+ cells at the focus of infection augments the effect of the chemotherapeutic agent.

The invention also provides a method of treating a disease, comprising administering a composition comprising Tat and Nef to alleviate a localized, detrimental infiltration of CD4+ cells occurring in association with a disease state. The site of administration of the composition comprising Tat and Nef may be in a different tissue or organ, for example, to promote T cell accumulation at a site less detrimental that that associated with the disease state. Alternately, administration may be systemic to cause CD4+ cells to leave peripheral tissue.

It is another object of the invention to treat individuals infected with HIV by inhibiting CD4+ cell extravasation with a systemically administered composition comprising Tat and Nef. It is another object of the invention to antagonize the chemotactic activity of the combination of Tat and Nef in an individual infected with HIV by providing antibodies to either or both of these proteins.

These and other objects of the invention are accomplished by the embodiments of the invention described below.

BRIEF DESCRIPTION OF THE FIGURES

FIG. 4D indicates the effect on chemotactic activity of media supplemented with syncytia-conditioned media in response to the addition of an antibody that binds Nef, "αNef."

DETAILED DESCRIPTION OF THE PREFERRED EMBODIMENTS

The Combination of Tat and Nef is a CD4+ Cell Chemoattractant

For the first time, it is possible to modulate CD4+ chemotaxis by promoting or antagonizing the chemotactic activity of the combination of Tat and Nef. Controlling CD4+ cell trafficking and infiltration in an individual opens many therapeutic possibilities, especially in treating diseases having a localized nature, as well as in providing treatment modes for individuals infected with HIV. In view of the activity of Tat and Nef in modulating localized accumulation of CD4+ cells, the invention provides methodology for promoting CD4+ cell chemotaxis to a localized site of infection as a means of augmenting the efficacy of extant chemotherapeutic methods. The invention further provides methodology for diverting CD4+ cell infiltration from a localized site where the presence of CD4+ cells is detrimental to the clinical outcome, by providing a composition comprising Tat and Nef at a distinct site, such as blood, within the individual where the accumulation of CD4+ cells is less detrimental.

Preferably, the present composition is administered in the presence of known chemotherapeutic agents as a means of augmenting their efficacy. For instance, a localized infection may be treated by the non-systemic injection of a composition comprising Tat and Nef at the site of infection in the presence of an antibiotic. The promotion of CD4+ cells to the site of infection will aid in the body's defense against the infection, enhancing the effect of the antibiotics.

"CD4+ cell" means a lymphocyte having cell surface CD4 molecules, as evidenced by binding of an antibody specific for CD4. An example of a suitable antibody is the monoclonal antibody OKT4 (Ortho Diagnostics, Piscataway, N.J.).

In Vitro Assay

An in vitro assay for determining the chemotactic activity of a test molecule is described in the Examples, below. This test was applied to various low molecular weight HIV proteins to determine which mimic the activity of the 30 kDa component of syncytium-conditioned media. The chemotactic activity of Rev, p24, Nef and Tat gradients was tested. Rev and p24 were neither chemotactic nor chemokinetic for CD4+ cells. Neither Nef alone nor Tat alone was chemotactic, but both were chemokinetic for these cells. Tat and Nef both stimulated single cell motility when added separately, resulting in a 50% increase in average instantaneous velocity in both cases.

Surprisingly, when Tat and Nef are added to the source well of the single-cell chemotaxis chamber, they function in combination as a chemoattractant. Antibodies to either Nef or Tat block the low molecular weight chemotactic activity, but not the chemokinetic activity, of media conditioned by HIV-induced syncytia. Thus, the low molecular weight chemotactic activity of syncytia-conditioned culture media comprises a gradient of Tat and Nef.

This activity of Tat and Nef is not the result of synergistic effects of the two molecules on chemotaxis, because one protein without the other is incapable of causing CD4+ cell chemotaxis. The requirement for both proteins for chemoattractant activity is believed to be an unusual, if not unprecedented, observation. Without being limited by theory, the data suggest that the two chemoattractants do not form a complex, such as a heterodimer, because this would affect their effective molecular weight during the formation of a chemotactic gradient. The molecular events involved in chemotaxis are complex, involving recognition of the chemotactic gradient, transmission of this recognition within the cell, and the actual generation of cellular motion. The precise events associated with chemotaxis in response to Tat and Nef are not fully understood. Tat and Nef may interact with the same or different cellular receptors, and the consequent cellular signaling pathway may converge upon a common intracellular target. The cellular receptor(s) that mediates chemotaxis may be the same or different from the receptor(s) that mediate chemokinetic stimulation.

The in vitro assay disclosed herein provides a preferred, routine means of assaying compounds for chemotactic activity for various cell types. The invention envisions the use of functional fragments and derivatives of Tat and Nef. "Functional fragments and derivatives" of Tat and Nef are defined as fragments and derivatives of these proteins that retain chemotactic activity toward CD4+ cells when used in combination. Functional activity may be assayed in the in vitro chemotaxis assay disclosed in the Examples. Fragments and derivatives of Tat and Nef may be produced by genetic engineering methods well known in the art, and expressed by the methods disclosed below.

In Vivo Assays

In addition to the in vitro assay described in detail below, animal models may be used to detect CD4+ cell chemoattractants. Like the Boyden assay, these in vivo assays may be hampered by the inability to discriminate between chemokinetic and chemotactic activities. Accordingly, the chemotactic activity of test components preferably is confirmed first by the in vitro assay described below before they are tested in vivo.

In vivo assays described in the art suggest the effectiveness of localized injection of putative T cell chemoattractants in promoting T cell extravasation and accumulation in peripheral tissue. Taub (1996). For example, localized CD4+ cell accumulation in vivo has been seen following injection of monocyte chemotactic proteins-1 (MCP-1), -2, or -3 and the cytokine RANTES (Regulated on Activation, Normal T Cell Expressed and Secreted). Taub et al. (1995); Murphy et al. (1994). Using animal models, the preferred routes of administration of the inventive composition may be determined. Animal models will also be useful in determining physiological doses of Tat and Nef effective to promote localized accumulation of CD4+ cells, as well as the optimal carriers, excipients, etc., for administration of the present composition.

Methods of Treating HIV Infection

Systemic infusion of a pharmaceutical composition comprising Tat and Nef can be useful in treating an individual infected with HIV. Peripherally located syncytia are expected to cause extravasation of CD4+ cells in response to the syncytium-induced concentration gradient of Tat and Nef. Recognition of a chemotactic gradient is required before leukocytes adhere to endothelial tissue and migrate through this tissue. Reviewed in Proost et al. (1996) and Jinquan et al. (1995). High systemic concentrations of Tat and Nef are expected to effectively mask a chemotactic gradient originating from peripheral tissue, thereby blocking the first, requisite step in leukocyte extravasation. In this manner, Tat and Nef may inhibit CD4+ cell extravasation and recruitment into syncytia. In light of the known chemotactic activity of gp120, the present pharmaceutical composition will be supplemented with a neutraizing antibody to gp120.

Preferably, systemic concentrations of Tat and Nef will be high enough to establish a chemical gradient sufficient to draw CD4+ cells out of lymph nodes and other peripheral tissue, increasing the number of circulating CD4+ cells. Localization of T cells in lymphoid tissue may contribute to the spread of HIV, because lymphoid tissue acts as a reservoir for HIV in an infected individual. Transmission of HIV may occur through routes other than syncytium formation, such as cell-to-cell transmission. Levy (1993). Accordingly, it is expected that decreasing the number of CD4+ cells in peripheral tissues, especially lymphoid tissue, will decrease viral burden by preventing T cell infection.

During the initial infection with HIV, plasma levels of HIV rise and CD4+ cell numbers fall. After a period of months, however, CD4+ cell numbers rebound and plasma HIV levels subside. The infection at this point is asymptomatic and is associated with a gradual decline in the number of CD4+ cells. Even though the rate of HIV replication is low during this period of "cellular latency," HIV infection is maintained by the integration of HIV genomes into the DNA of target cells. The development of AIDS follows this period of cellular latency. The onset of AIDS is correlated with the switch from NSI to SI HIV variants, as described above, and the rapid fall of CD4+ cell counts.

Nef and Tat have been implicated as factors possibly involved in regulating cellular latency. While there is some evidence that Nef may maintain cellular latency, Tat, in fact, may have the opposite effect. Reviewed in Levy (1993). Thus, it is possible that infusion of Tat and Nef by themselves into an HIV infected individual may activate latently infected cells, promoting viral replication and the onset of AIDS. Accordingly, the present composition is preferably administered in conjunction with chemotherapeutic agents effective to inhibit HIV replication. In a preferred embodiment, HIV replication is inhibited by co-administration of the present composition with highly active anti-retroviral therapy (HAART) as described in Berger et al. (1998), herein incorporated by reference.

Cellular latency persists only for the life time of the cells harboring the HIV genome. One strategy for HIV chemotherapy has been to deliberately activate HIV replication in latently infected cells to expose HIV to a battery of existing chemotherapeutic agents effective at inhibiting viral replication. See U.S. Pat. No. 5,747,526 for a general discussion of known HIV chemotherapies. The desired result of this approach is the depletion of the reservoir of HIV in latently infected cells. The combination of IL-2, IL-6, and tumor necrosis factor-$\alpha$ (TNF-$\alpha$) is preferred for activating latently infected CD4+ cells. Chun et al. (1998).

Because the administration of Tat and Nef may activate latent cells, it may be possible to use these compounds to deplete the reservoir of HIV as described above. Accordingly, in one embodiment of the invention, Tat and Nef are administered systemically, either as a steady infusion or as a bolus, to an individual latently infected with HIV in order to activate latently infected cells, wherein Tat and Nef are added concurrently with chemotherapeutic agents effective at inhibiting HIV replication. In a preferred embodiment, Tat and Nef are administered in association with HAART.

Antibodies Against Tat and Nef

The present invention envisions the use of antibodies directed against Tat and Nef as antagonists of chemotaxis, in combination with a neutralizing antibody directed against gp120. Antibodies that recognize these proteins are disclosed in U.S. Pat. No. 5,606,026, for example, herein incorporated by reference. The invention provides a method for administering the antibodies to inhibit the chemotactic activity of Tat or Nef and gp120 by reducing their systemic concentration. In a preferred embodiment, neutralizing antibodies directed against Tat and Nef and gp120 are administered in combination with compounds known to activate latently infected cells, such as IL-1, and chemotherapeutic agents effective to inhibit viral replication. In this embodiment, anti-Tat and anti-Nef antibodies, in combination with anti-gp120 antibodies, reduce the cell-to-cell transmission of HIV via syncytia, while IL-1 activates latently infected cells, and HAART suppresses production of infectious HIV.

Antibodies against Tat and/or Nef may be raised by using Tat and/or Nef as vaccine components in the form of intact proteins, or as antigenic fragments. In another embodiment, antibodies against Tat and/or Nef may be raised intracellularly using the procedures disclosed, for example, in U.S. Pat. No. 5,851,829 or Chen et al. (1994).

Vaccine Supplementation with Tat and Nef

Vaccine efficacy may be boosted by the recruitment of CD4+ cells to the site of vaccine injection. Accordingly, the present invention provides a method of boosting vaccine efficacy by providing Tat and Nef as components of a vaccine. The chemotactic activity of Tat and Nef will provoke accumulation of CD4+ cells to the injection site.

CD4+ cells recruited from the circulation contain naïve Th0 cells, which differentiate into Th1 and Th2 cells that mediate cellular and humoral immune reaction, respectively. The pathway of Th0 cell differentiation has been shown to be effected by particular cytokines. Accordingly, the addition of these cytokines as additional vaccine components may enhance the effect of Tat and Nef by biasing immunity against the antigen as either cellular immunity or humoral immunity. Cellular immunity is desirable for treatment of intracellular parasitic infection. Differentiation of Th0 cells into Th1 cells may be stimulated by a neutralizing antibody directed against interleukin4 ($\alpha$-IL-4) or by the addition of IL-12. Alternately, humoral immunity is desirable for the treatment of infection by extracellular agents, such as nematodes. Th2 cell differentiation may be stimulated by IL-4 or $\alpha$-interferon $\gamma$. Sher et al. (1992); Clerici et al. (1993); Desmedt et al. (1998); Silva-Teixeira et al. (1998).

Methods of Treating Disease States Comprising Chemotaxis of CD4+ Cells

CD4+ cell infiltration in response to inflammatory stimuli is involved in a large number of disease states. These diseases include, but are not limited to, inflammatory bowel disease, bacterial infection, viral infection, atherosclerosis, asthma, graft versus host disease (GVHD), endotoxemia, uveoretinitis, granulomatous diseases, and psoriasis. Center (1996); Jinquan et al. (1995); Taub (1996); Van de Kerkhof et al. (1996).

The present invention provides for provoking CD4+ cell infiltration and accumulation at peripheral sites where the accumulation of CD4+ cells is desirable. Such sites may be localized sites of infection, for example. The present composition is preferably administered in conjunction with antibiotics to promote treatment of the infection. For example, to provide CD4+ cell accumulation in the respiratory tract to promote clearance of *Cryptococcus neoformans* infections, the present composition may be administered as an aerosol to the afflicted area. Huffnagle et al. (1995).

When CD4+ cells infiltration is undesirable at a particular site, such as in inflammatory diseases, the present composition may be used to divert CD4+ cells to other areas. For example, the present composition may be added systemically in sufficient amounts to cause CD4+ cells to enter the circulation, thereby lowering the peripheral counts of these cells. Alternately, the present composition may be administered to a different peripheral location, such as a different organ, less likely cause inflammatory complications for the patient, causing a diversion of CD4+ cells from the site of inflammation.

The invention envisions irrigating body areas or organs with the present composition as a means of depleting the local count of CD4+ cells. Exfiltration of CD4+ cells from foreign tissue, such as bone marrow, may be desirable as a means to providing a pool of CD4+ cells that may be transplanted into a patient to selectively reconstitute CD4+ cells, such as an individual undergoing chemotherapy and or an HIV-infected individual. Depleting CD4+ cells in an organ may also be desirable if the organ is to be transplanted, in order to ameliorate complications such as GVHD.

Pharmaceutical Compositions and Routes of Administration

Pharmaceutical compositions comprising Tat and Nef can be formulated and administered according to well known methods. Tat and Nef, or their functional fragments or derivatives, may be admixed with a pharmaceutically acceptable carrier vehicle. Suitable vehicles and their formulation, inclusive of other human proteins, e.g., human serum albumin, are described, for example, in *Remington's Pharmaceutical Sciences* (16th ed., Osol, A., Ed., Mack, Easton Pa. (1980)). In order to form a pharmaceutically acceptable composition suitable for effective administration, such compositions will contain an effective amount of Tat and Nef proteins, together with a suitable amount of carrier vehicle.

Pharmaceutical compositions for use in accordance with the present invention may be formulated in conventional manner using one or more physiologically acceptable carriers or excipients. Thus, the compounds and their physiologically acceptable salts may be formulated for administration by a variety of routes. The compounds may be delivered by parenteral, inhalation or insulation (either through the mouth or the nose), topical, oral, or depot administration.

The compounds may be formulated for parenteral administration by injection, e.g., by bolus injection, repeated injections, or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use. Instead of injection, the compounds may be administered as an irrigation fluid used to wash areas or organs of the body.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g. gelatin for use in an inhaler or insufflator may be formulated containing a powder mix of the compound and a suitable powder base such as lactose or starch.

Formulations and methodology for administering proteins by inhalation of an individual are known in the art and are described, for example, in U.S. Pat. No. 5,320,094. This patent describes delivery of a therapeutically effective amount of a protein into the lungs of an individual. The protein is aerosolised and delivered at a regulated flow rate below 30 liters/min. The described methodology is effective to deliver up to 90% of the aerosolised protein into the lungs.

In addition to the formulations described previously, the compounds may also be formulated as a depot preparation. Such long acting formulations may be administered by implantation (for example subcutaneously or intramuscularly) or by intramuscular injection. The compounds may also be formulated in rectal compositions such as suppositories or retention enemas, e.g., containing conventional suppository bases such as cocoa butter or other glycerides.

Topically administered formulations may be in the form of ointments and may contain pharmaceutically acceptable antibiotics, emollients, and stabilizers. A composition comprising Tat and Nef may be administered topically on a surgical apparatus, such as a bandage, gauze, foam, or surgical instrument.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated or formulated for sustained release by methods well known in the art. Liquid preparations for oral administration may take the form of, for example, solutions, syrups or suspensions, or they maybe presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g. lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preferred formulations for oral delivery are described by U.S. Pat. Nos. 5,574,018 and 5,428,023. Biologically active conjugates of a therapeutically useful protein are made with vitamin $B_{12}$ ($VB_{12}$) by covalently binding the primary (5') hydroxyl group of the ribose moiety of $VB_{12}$ to the therapeutic protein. When the resulting conjugate is orally delivered, it binds intrinsic factor (IF) transporter protein in the gastrointestinal tract and is then taken up through the epithelium into the bloodstream, retaining the biological activity of the protein therapeutic. The conjugates may be orally administered in the presence of purified IF, resulting in greater absorption.

WO 93/25221 describes compositions formulated for oral delivery, comprising therapeutic proteins contained in microspheres made of protein and/or synthetic polymer. The microspheres protect their protein contents against gastrointestinal proteases and provide controlled and sustained release of their contents. Microspheres can be designed to pass through the intestinal epithelium into the blood or lymph, and they may be targeted to particular cells or organs. Formulations and methodology useful for targeting orally administered microparticles to various organs are described in EP 531,497, for example.

Protein Expression

A particular advantage of the present invention is the provision of Tat and Nef in the form of recombinantly produced proteins, which can be produced relatively easily and inexpensively. Tat and Nef can be expressed recombinantly using known methods well known in the art. Tat and Nef can be expressed in a modified form, such as a fusion protein, and can include not only secretion signals, but also additional heterologous functional regions. For instance, a region of additional amino acids, particularly charged amino acids, can be added to the N-terminus of a polypeptide to improve stability and persistence in the host cell, during purification, or during subsequent handling and storage. Also, peptide moieties can be added to a polypeptide to facilitate purification. Such regions can be removed prior to final preparation of a polypeptide. The addition of peptide moieties to polypeptides to engender secretion or excretion, to improve stability and to facilitate purification, among others, are familiar and routine techniques in the art. Such methods are described in many standard laboratory manuals, such as Sambrook et al. (1989) *Molecular Cloning: A Laboratory Manual,* 2d ed., CSHL Press, NY, Chapters 17.29–17.42 and 18.1–18.74.

The present invention, thus generally described, will be understood more readily by reference to the following examples, which are provided by way of illustration and are not intended to be limiting of the present invention.

EXAMPLE 1

Preparation and Culture of T Cells

To obtain a highly enriched culture of CD4+ peripheral blood T cells, 250 ml of fresh blood was drawn from a healthy, HIV-negative donor into heparinized syringes. 31 ml were overlaid on 15 ml of Ficoll-Hypaque cushion solution in each of eight 50 ml conical tubes. The tubes were centrifuged 40 min at 550×g, and the band of mononuclear cells atop each cushion was retrieved and pooled into a fresh 50 ml conical tube. The cells were pelleted at 1,000×g for 10 min and washed 3 times in Earle's Balanced Salts Solution (EBSS). The final pellet was resuspended in 40 ml of RPMI 1640 (Gibco) supplemented with 10% heat-inactivated fetal bovine serum (FBS), 2 mM L-glutamine, 1×MEM non-essential amino acid solution, 1 mM sodium pyruvate, 100 U/ml penicillin and 100 $\mu$g/ml streptomycin sulfate. The cell suspension was transferred to a T-75 culture flask and incubated for 2 h at 37° C. in 5% $CO_2$. Non-adherent cells were transferred to a 50 ml conical tube, gently pelleted, resuspended in EBSS, and counted. Shutt et al. (1995). $1.25\times10^8$ cells were passed through a CELLECT column (Biotex Laboratories, Inc., Edmonton, Canada), according to the manufacturer's protocol. CELLECT columns preferentially allow flow-through of CD4+ cells by retaining CD8+ and B cells. Alternately, using the same principal of selective adsorption, CD4+ cells were purified by magnetic bead separation with kits provided by Miltenyi. The purified CD4+ cells were pelleted, resuspended at a final concentration of $2\times10^6$/ml in RPMI 1640 medium supplemented as above, but with an additional 10% FBS, 10 $\mu$g/ml phytohemagglutinin and 10 U/ml IL-2, from which lectin contaminants had been removed. Before use in the chemotaxis experiments, the CD4+ blood cells were grown in this medium for a minimum of 72 hrs. Cells of the immortalized SupT1 cell line were maintained according to methods previously described. Smith et al. (1984); Sylwester et al. (1993).

EXAMPLE 2

Infection with HIV and Obtaining Syncytium-Conditioned Supernatant

HIV-1LAI (previously referred to as HTLV-IIIB) was passed in cell cultures according to methods previously described. Harada et al. (1985). For infection, $10^7$ SupT1 cells were pelleted, resuspended in 1 ml of infected culture supernatant containing 500 $TCID_{50}$ doses of HIV-1LAI, and incubated for 2 h. Parallel mock infections were performed by resuspending the cells in medium without virus. After incubation, cells were diluted with fresh medium. To obtain syncytium-conditioned supernatant, 72 to 96 hour post-infected cultures were placed on the stage of an inverted microscope inside a biosafety cabinet, and individual syncytia were picked with a micropipettor and placed in a 1.5 ml screw cap tube with fresh medium. The syncytia conditioned the media for 6 hours, after which time the syncytia were centrifuged and the supernatant was removed to a fresh tube and stored at –80° C.

EXAMPLE 3

Setting up the Chemotaxis Chamber

Cultures of SupT1 or CD4+ blood cells were grown to a density of $1\times10^6$ cells/ml, and 200 $\mu$l of the culture were seeded onto the centers of 22×30 mm THERMANOX® plastic coverslips inside of plastic petri dishes, and were incubated overnight. This step conditioned the surface of the coverslip, increasing the proportion of motile cells approximately four-fold. Inside the biosafety cabinet, excess medium was removed from the coverslip, and the conditioned side of the coverslip was placed onto the center of the chamber and clamped down. The chamber was then inverted so that cell motility could be measured by their movement over the conditioned, plastic coverslip. The source and sink wells were simultaneously filled with the test solutions indicated below. "EBSS" is Earle's Balanced Salt Solution. "Nhs" is normal human serum. "SCM" is medium conditioned by HIV-induced syncytia. "Cond. Med." is medium conditioned by uninfected cells. A glass coverslip was placed over the wells and bridge, first over the sink, then in the direction to the source, to minimize contamination of the sink solution with the source solution. The chamber was then placed on the stage of the microscope as described below.

EXAMPLE 4

Behavioral Analysis of Cells

Figure 2:
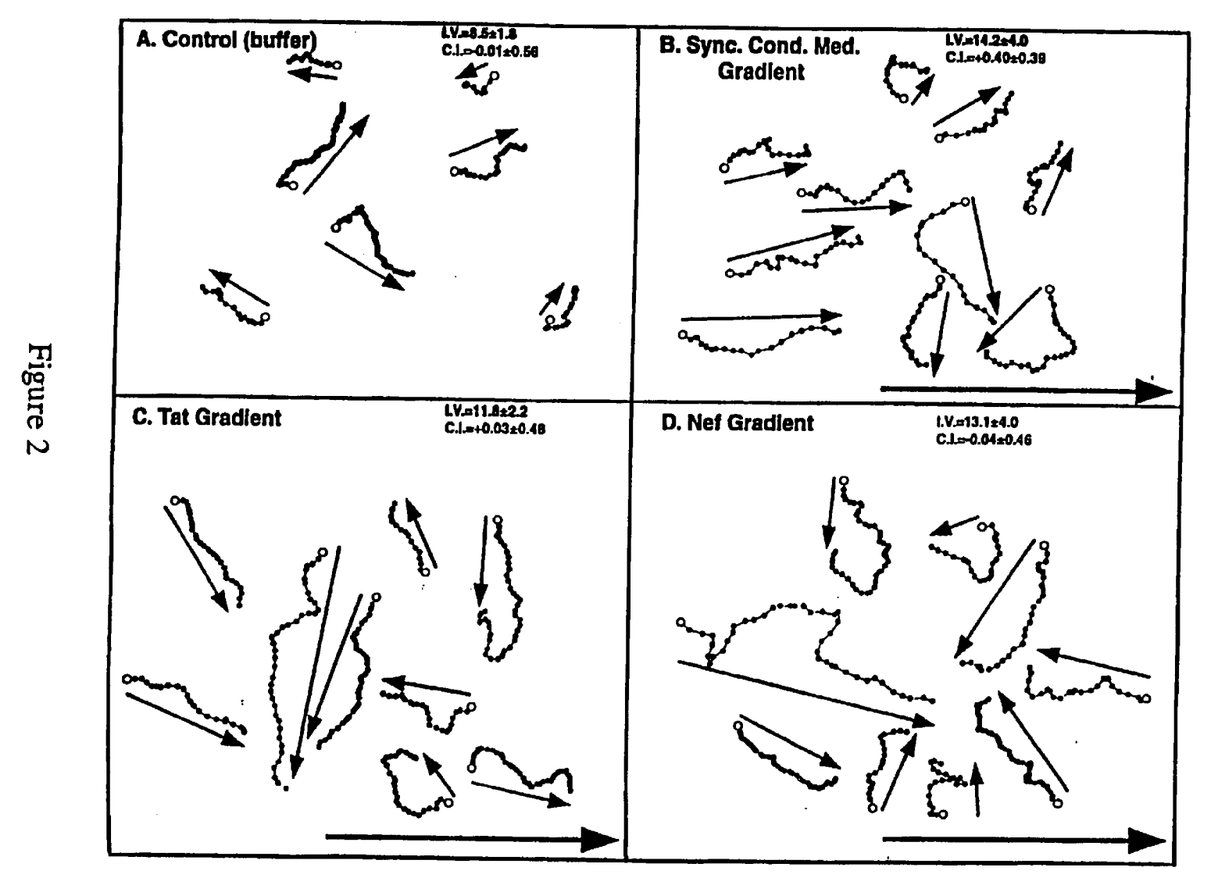
FIGS. 2A–D show representative time-dependent tracks of CD4+ cells exposed to the indicated gradients. The direction of the concentration gradient is indicated by the heavy arrows.

The motile behavior of both cells and HIV-induced syncytia were analyzed with the DIAS software program according to methods previously described. Soll (1995). The chemotaxis chamber containing the cells and source and sink solutions was positioned on a Zeiss AXOIVERT 100 microscope equipped with long-distance objectives and condenser. The image from a COHU video camera of cells on the bridge of the chamber was digitized directly into a computer. Temperature was maintained at 37±1° C. with a thermostatically controlled stage heater. Video images of single cell movements were plotted and digitized by the method of Shutt et al. (1995). The time-dependent location of each cell, or "centroid," was plotted, as shown in FIG. 2, and instantaneous cellular velocities were computed for each centroid by the method of Soll (1995) and Shutt et al. (1995). Other parameters, including directional change, were computed according to methods previously described. Soll (1995) and Shutt et al. (1995). A cell moving continuously in a straight line exhibits a directional change value of 0 degrees. Chemotactic index was computed as the 'chemotropism ratio' of McCutcheon (1944), which is the distance moved toward the source divided by the total distance moved. The proportion of chemotactically responsive cells (CP+) was computed by dividing the number of cells with a positive chemotactic index by the total number of cells and was expressed as a percentage.

EXAMPLE 5

Characterizing the Chemotactic Chamber

Using the described chamber, chemotaxis was analyzed for gradients of high molecular weight molecules. Shutt et al. (1998). The time required for gradient formation is proportional to the molecular weight of the chemoattractant. Tanford (1961). The chamber could then be characterized by measuring the time required for maximal cellular response to a number of known chemotactic and chemokinetic agents. Maximum response time was then plotted against molecular weight to obtain a plot that could be used to generate a standard curve to estimate the molecular weight of an unknown chemotactic or chemokinetic agent. See FIG. 1A.

EXAMPLE 6

Distinguishing Chemotaxis from Chemokinesis

Since single cell behavior is not assessed in Boyden chambers during the actual process of migration, there has been some concern that some agents interpreted by this method as chemoattractants may in fact be only chemokinetic agents. Zigmond et al. (1973); Rhodes (1982); Wilkinson (1988). There are computational methods to correct for this deficiency, but even when such an analysis is performed, there remain problems of data interpretation. In addition, because the Boyden chamber provides only an endpoint of the number of cells on a particular side of the chamber, it does not assess the behavior of the test population. By continuously video recording individual cells at the bridge of the described chemotaxis chamber, the behavior of every cell is continuously recorded and can then be digitized into the computer-assisted DIAS motion analysis system to assess chemokinetic and chemotactic responses over time. Cells responding chemokinetically but not chemotactically to a stimulatory molecule will exhibit an average instantaneous velocity (I.V.) at optimum concentration significantly higher than that of cells in buffer, but will never exhibit a chemotactic index (C.I.) significantly different from 0.00, or a percent positive chemotaxis index (CP+) significantly different from 50%. Cells responding chemotactically but not chemokinetically to a stimulatory molecule will exhibit an average I.V. that is not significantly different from that in buffer, but will exhibit an average C.I. and CP+ significantly greater than 0.00 and 50%, respectively.

EXAMPLE 7

HIV-Induced T Cell Syncytia Release Two T Cell Chemoattractants

Figure 1:
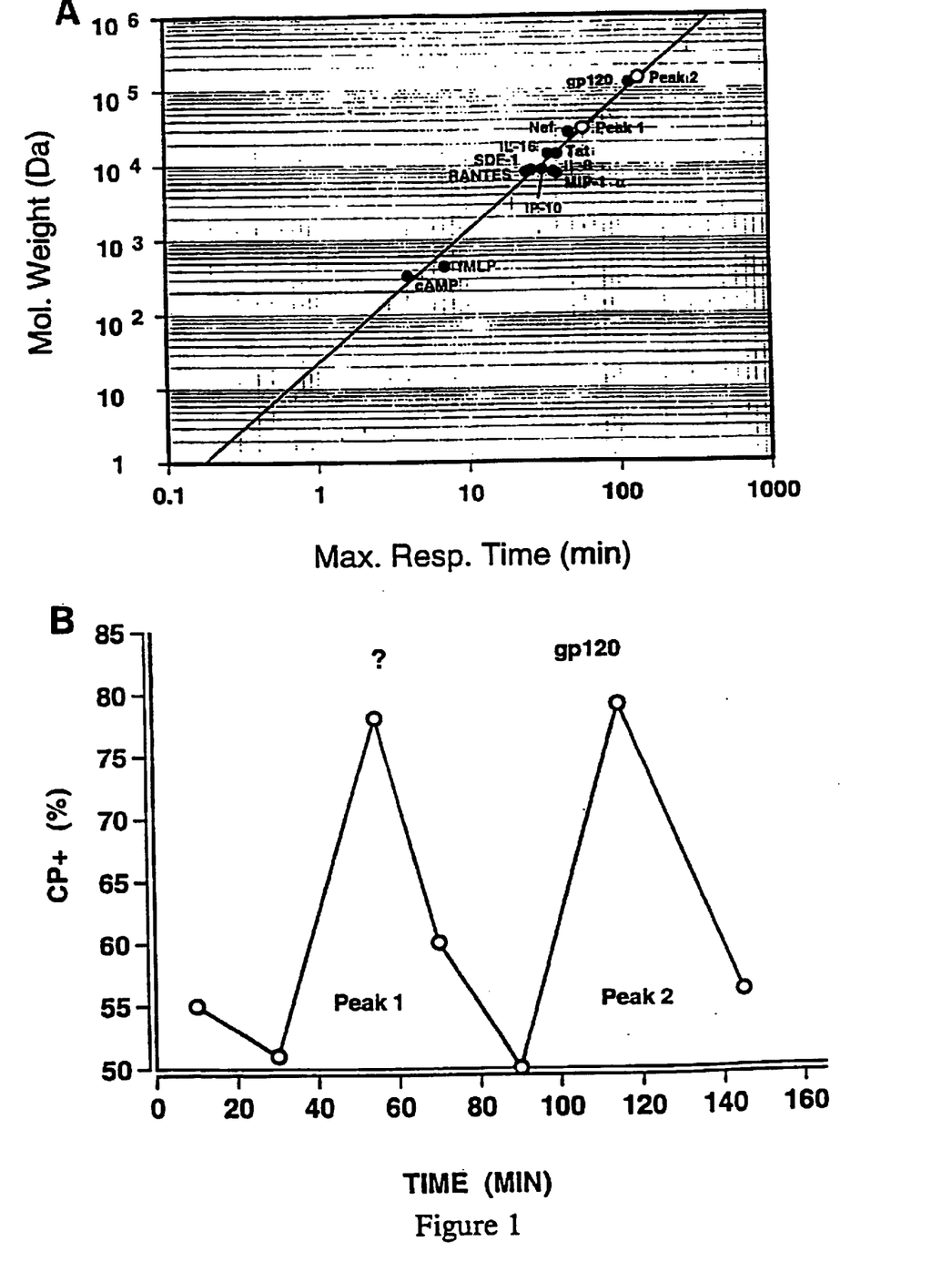
FIG. 1A shows the calibration curve determined by measuring the response time of known CD4+ chemoattractants, using the single-cell chemotaxis chamber disclosed by Shutt et al. (1998). Response times determined for peak 1 and peak 2 of syncytia-conditioned culture medium are indicated.
FIG. 1B shows the proportion of chemotactically responsive cells (CP+) as a function of time following establishment of a gradient in the single-cell chemotaxis chamber. Peaks 1 and 2 of syncytia-conditioned culture medium are indicated.

Using the single cell chemotaxis chamber, we previously demonstrated that HIV-induced T cell syncytia release two chemoattractants, one exerting a maximum effect at approximately 55 minutes and the other at approximately 115 minutes (Figure B). Shutt et al. (1998). Polyethylene glycol (PEG)-induced T cell syncytia, which mimic the organization and behavior of HIV-induced T cell syncytia, do not release either attractant, suggesting that both attractants are related to viral infection. Id. The molecular weights of the two attractants were estimated to be roughly 30 and 120 kDa (FIG. 1A). The latter attractant was demonstrated by antibody-blocking experiments to be gp120, and purified gp120 was demonstrated to be a chemoattractant. Id. Both the high and low molecular weight chemoattractants also apparently had a chemokinetic effect on peripheral blood T cells. Id.

EXAMPLE 8

Individually, Nef and Tat are Chemokinetic, but not Chemotactic, Stimulators of CD4+ Cells The absence of chemoattractants in the supernatant of PEG-induced syncytia suggested that the chemoattractants released from HIV-induced syncytia were encoded by the virus. This proved true for the 120 kDa attractant. Id. We, therefore, tested whether the low molecular weight virally encoded proteins Rev, p24, Nef and Tat functioned as chemoattractants. Neither Rev, a regulator of viral gene expression, nor p24, a capsid protein, stimulated chemoattraction (Table 1) or chemokinesis (Table 2) in twice the time required for these molecules to generate a gradient in the chamber.

Neither Tat nor Nef functioned as chemoattractants (Table 1). However, both of these latter proteins potently stimulated chemokinesis (Table 2). While the proportion of motile cells in buffer was 51% and the average instantaneous velocity was 8.3±2.3 µm per mm, the proportion of motile cells in a gradient of Tat was 61% and the average instantaneous velocity was 12.9±3.7 µm per min (Table 2), and the proportion of motile cells in a gradient of Nef was 65% and the average instantaneous velocity was 11.3±2.8 µm per min. In FIG. 2, centroid tracks are presented of cells moving in buffer, in a gradient of the low molecular weight chemoattractant of HIV-induced syncytium-conditioned supernatant, in a gradient of Tat and in a gradient of Nef. The centroid tracks of cells in buffer (FIG. 2A) are short, while those of cells in the syncytium supernatant gradient (FIG. 2B), the Tat gradient (FIG. 2C) and the Nef gradient (FIG. 2D) are longer. However, while the majority of translocation vectors (75%) point in the direction of increasing syncytium supernatant chemoattractant (FIG. 2B), the proportion of vectors pointing in the direction of increasing concentration in the Tat and Nef gradients were 33% and 44%, respectively. Together, these results demonstrate that Tat and Nef function as potent chemokinetic stimulants of CD4+ cells, but they do not function as chemoattractants.

EXAMPLE 10

A Combination of Tat and Nef Functions as a Chemoattractant of T Cells

Figure 3:
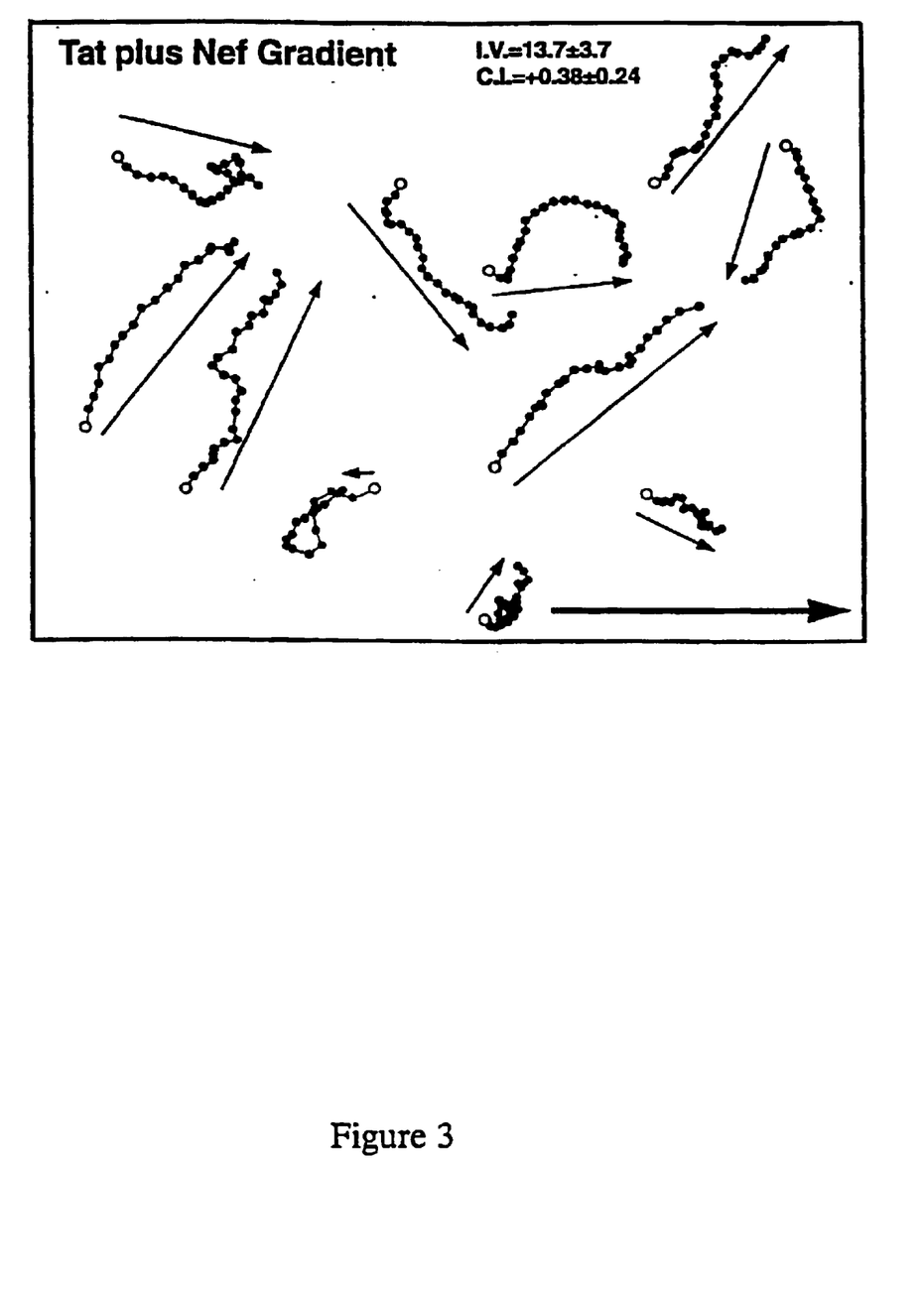
FIG. 3 shows representative time-dependent cellular tracks in the presence of a gradient of purified Tat and Nef.

To test whether the chemokinetic stimulation of T cell motility by Tat and Nef was additive or synergistic, cells were analyzed in combined gradients. The average instantaneous velocity of CD4+ cells in the combined gradients was similar to that in either the Tat or Nef gradient alone (Table 2). Surprisingly, however, cells now chemotaxed towards the source of the two gradients. The average chemotactic index in the Tat plus Nef gradients was 0.35±0.43, which was highly similar to the chemotactic index of +0.31±0.49 in a gradient of the lower molecular weight chemoattractant of syncytium supernatant. Both of these C.I.s contrasted markedly with the average C.I.s in buffer (+0.08±0.55), in a gradient of Tat alone (+0.06±0.49) or in a gradient of Nef alone (−0.06±0.46) (Table 1). The CP+ in the Tat plus Nef gradients was 80%, which was similar to the CP+ of 78% in a gradient of the lower molecular weight chemoattractant of syncytium supernatant. Both of these CP+s contrasted markedly with the CP+s in buffer (54%), in a gradient of Tat alone (40%) or in a gradient of Nef alone (37%) (Table 1). In FIG. 3, an example is presented of cell tracks in a combination gradient of Tat and Nef. Note that the majority of direction vectors (80%) point in the direction of increasing concentration and that the tracks are long (compared to tracks in buffer, FIG. 2A), reflecting both chemoattractant and chemokinetic stimulation.

EXAMPLE 11

Figure 4:
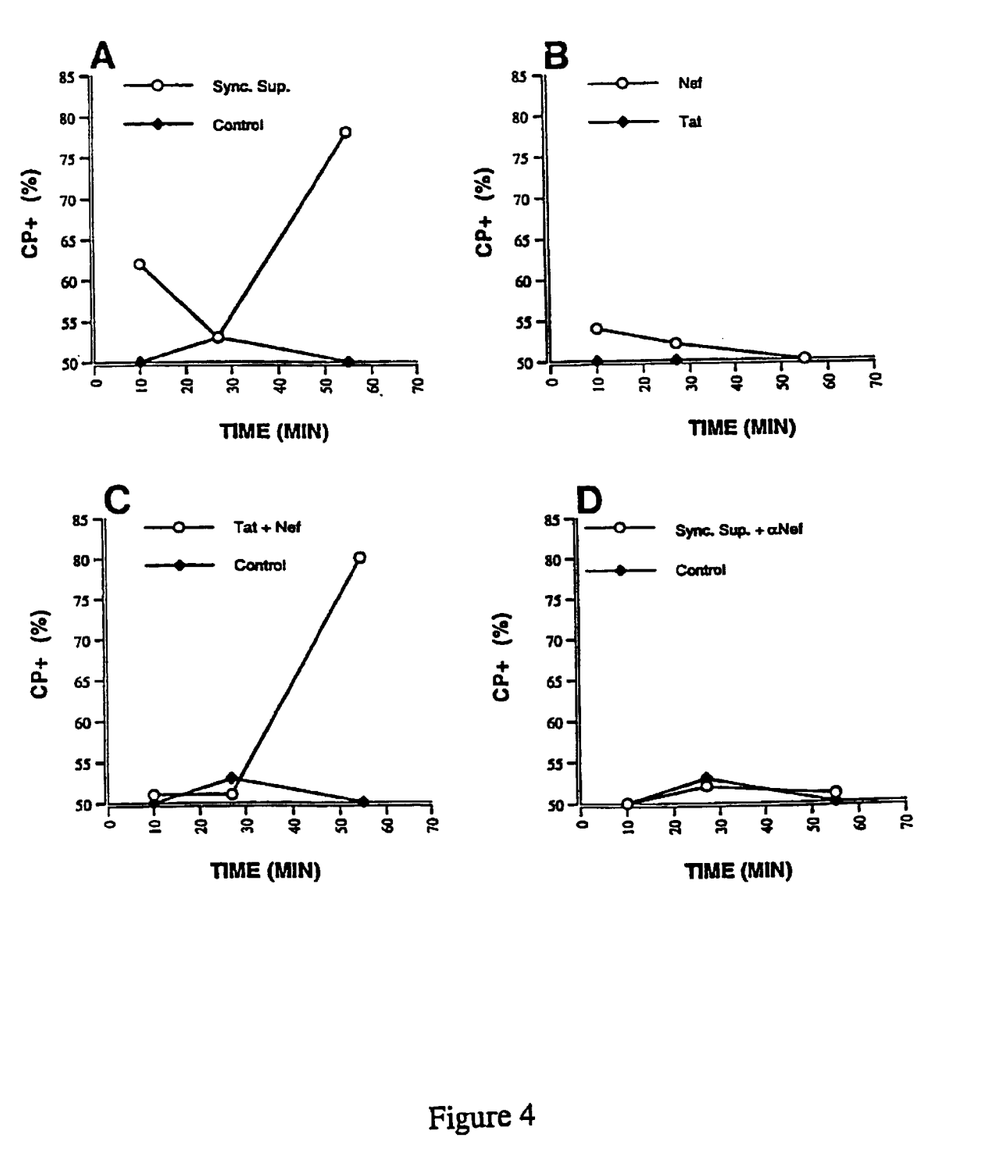
FIGS. 4A–D show CP+ as a function of time for the indicated media components.

Nef and Tat Represent the Low Molecular Weight Chemoattractant in Medium Conditioned by HIV-Induced T Cell Syncytia The low molecular weight chemoattractant activity in medium conditioned by HIV-induced T cell syncytia peaked at approximately 55 min, resulting in an estimated molecular weight of approximately 30 kDa. To test whether Tat and Nef functioned in combination as the low molecular weight chemoattractant, blocking experiments were performed in which anti-Tat and/or anti-Nef antibody were added to HIV-induced syncytium-conditioned medium and the CP+ monitored with time for 55 min. In buffer alone, the CP+ remained close to 50% throughout the 55 min period of analysis (FIG. 4A). In a gradient of syncytium supernatant, the CP+ increased to 75% at 55 min (FIG. 4A). In a gradient of Nef or Tat, the CP+ remained close to 50% throughout the 55 min period of analysis (FIG. 4C), but in a gradient of Nef plus Tat, the CP+ increased to 80% after 55 min (FIG. 4C). In a gradient of syncytium supernatant containing anti-Nef antibody, the CP+ remained close to 50% (FIG. 4D). An anti-Nef antibody, therefore, blocked the chemotactic activity of syncytium supernatant at 55 min. But it did not block chemokinetic activity at 55 mm, which was similar to that of syncytium supernatant in the absence of antibody, Tat alone, Nef alone or Tat plus Nef (Table 2). Similar results were obtained using an anti-Tat antibody (Table 2).

TABLE 1

Chemotactic response of peripheral blood CD4+ cells

| Sink | Source | N | 55 min CP+ (%) | C.I. |
|---|---|---|---|---|
| Cond. Med. | Sync. Cond. Medium (SCM) | 27 | 78% | +0.313 ± 0.486 |
| EBSS + 2% nhs | EBSS + 2% nhs | 28 | 54% | +0.079 ± 0.554 |
| EBSS + 2% nhs | P24 | 20 | 60% | +0.067 ± 0.434 |
| EBSS + 2% nhs | Rev | 14 | 36% | +0.060 ± 0.458 |
| EBSS + 2% nhs | Tat | 20 | 40% | +0.060 ± 0.488 |
| EBSS + 2% nhs | Nef | 19 | 37% | +0.061 ± 0.462 |
| EBSS + 2% nhs | Tat + Nef | 40 | 80% | +0.345 ± 0.425 |
| EBSS + 2% nhs | SCM + anti-Nef | 16 | 50% | +0.016 ± 0.470 |
| Cond. Med. | SCM + anti-Tat | 20 | 45% | −0.016 ± 0.483 |
| Cond. Med. | SCM + anti-Tat + anti-Nef | 18 | 44% | −0.007 ± 0.494 |
| EBSS + 2% nhs | Tat + Nef + anti-Tat + anti-Nef | 20 | 40% | −0.111 ± 0.495 |

TABLE 2

Chemokinetic response of peripheral blood CD4+ cells

| Sink | Source | N Analyzed | Inst. Vel. (micron/min) | Motile Cells (%) |
|---|---|---|---|---|
| Cond. Med. | SCM | 27 | 13.3 ± 3.9 | 87% |
| EBSS + 2% nhs | EBSS + 2% nhs | 28 | 8.3 ± 2.3 | 51% |
| EBSS + 2% nhs | p24 | 20 | 6.5 ± 2.4 | 52% |
| EBSS + 2% nhs | Rev | 14 | 8.5 ± 3.7 | 55% |
| EBSS + 2% nhs | Tat | 20 | 12.9 ± 3.7 | 61% |
| EBSS + 2% nhs | Nef | 19 | 11.3 ± 2.8 | 65% |
| EBSS + 2% nhs | Tat + Nef | 40 | 12.1 ± 4.1 | 86% |
| Cond. Med. | SCM + anti-Nef | 16 | 12.4 ± 3.9 | 67% |
| Cond. Med. | SCM + anti-Tat | 20 | 16.9 ± 4.9 | 84% |
| Cond. Med. | SCM + anti-Tat + anti-Nef | 18 | 16.2 ± 5.4 | 79% |
| EBSS + 2% nhs | Tat + Nef + anti-Tat + anti-Nef | 20 | 12.8 ± 4.1 | 68% |

BIBLIOGRAPHY

Benichou et al. (1994) *J. Biol. Chem.* 269:30073–30076.
Berger et al. (1998) *Proc. Natl. Acad. Sci. USA* 95:11511–11513.
Boyden (1962) *J. Exp. Med.* 115:453–466.
Center (1996) *Immunol. Today* 17:476–481.
Chen et al. (1994) *Human Gene Therapy* 5:595–601.
Chun et al. (1998) *J. Exp. Med.* 188:83–91.
Clerici et al. (1993) *Immunol. Today* 14:107–111.
Desmedt et al. (1998) *J. Immunol.* 160:5300–5308.
Frankel et al. (1996) *Science* 272:115–117.
Gelderblom et al. (1985) *Lancet* 2:1016–1017.
Gratton et al. (1996) *J. Immunol.* 157:3305–3311.
Harada et al. (1985) *Science* 229:563–566.
Huffnagle et al. (1995) *J. Immunol.* 155:4790–4797.
Jinquan et al. (1995) *Exp. Dermatol.* 4:281–290.
Kowolski et al. (1987) *Science* 237:1351–1355.
Levy (1993) *Microbiological Rev.* 57:183–289.
Lifson et al. (1986a) *Nature* 323:725–728.
Lifson et al. (1986b) *Science* 232:1123–1127.
McCutcheon (1944) *Physiol. Rev.* 26:319.
McDougal et al. (1986) *Science* 231:382–385.
Miedema (1992) *Immunodeficiency Rev.* 3:173–193.
Murphy et al. (1994) *Eur. J. Immunol.* 24:1823–1827.
Otake et al. (1994) *J. Immuno.* 153:5826–5837.
Proost et al. (1996) *Int. J. Clin. Lab. Res.* 26:211–223.
Rhodes (1982) *J. Immunol. Methods* 49:235–236.
Richman et al. (1994) *J. Infect. Diseases* 169:968–974.
Ryan et al. (1995) *J. Biol. Chem.* 270:17081–17086.
Sambrook et al. (1989) *Molecular Cloning: A Laboratory Manual*, 2d ed., CSHL Press, NY.
Schneider et al. (1986) *J. Gen. Virol.* 67:2533–2538.
Sher et al. (1992) *Ann. Rev. Immunol.* 10:385–409.
Shutt et al. (1995) *Cell. Immuno.* 166:261–274.
Shutt et al. (1998) *J. Cell Sci.* 111:99–109.
Silva-Teixeira et al. (1998) *Hum. Immunol.* 59:219–224.
Smith et al. (1984) *Cancer Res.* 44:5657–5660.
Soll (1995) *Int. Rev. Cytol.* 163:43–104.
Staniford (1997) *Curr. Opin. Pulmon. Med.* 3:81–88.
Sylwester et al. (1993) *J. Cell Sci.* 106:941–953.
Sylwester et al. (1995) *AIDS Res. Human Retrovir.* 11:433–441.
Sylwester et al. (1997) *J. Immunology* 158:3996–4007.
Sylwester et al. (1998) *J. Leukocyte Biol.* 63:233–244.
Tanford (1961) In *Physical Chemistry of Molecules*, Wiley, NY.
Taub et al. (1995) *J. Clin. Inves.* 95:1370–1376.
Taub (1996) *Cytokine & Growth Factor Reviews* 7:355–376.
Van de Kerkhof et al. (1996) *Clin. Exp. Dermatol.* 21:325–329.
Van Deventer et al. (1997) *Pharm. World Sci.* 19:55–59.
Wessels et al. (1989) *J. Cell Biol.* 109:2841–2851.
Wilkinson (1998) *Methods Enzymol.* 162:38–50.
Zigmond et al. (1973) *J. Exp. Med.* 137:387–410.
Zigmond (1978) In Leukoctye Chemotaxis Methods, Physiology and Clinical Implication (Gallin et al., eds.) Raven Press, NY.

What is claimed is:

1. A pharmaceutical composition comprising purified Tat and Nef in an effective amount to promote localized accumulation of CD4+ cells, and an antimicrobial chemotherapeutic agent.

2. The pharmaceutical composition of claim 1, further comprising a pharmacologically acceptable diluent, carrier, stabilizer, or excipient.

3. The pharmaceutical composition of claim 1, wherein said antimicrobial chemotherapeutic agent is an antibiotic.

4. The pharmaceutical composition of claim 1, wherein said antimicrobial chemotherapeutic agent is a compound effective at inhibiting HIV replication.

5. The pharmaceutical composition of claim 4, wherein said chemotherapeutic agent is a component of highly active anti-retroviral therapy (HAART).

6. The pharmaceutical composition of claim 4, wherein said pharmaceutical composition further comprises interleukin-2 (IL-2) and IL-6.

7. The pharmaceutical composition of claim 6, wherein said pharmaceutical composition further comprises tumor necrosis factor-α (TNF-α).

* * * * *

UNITED STATES PATENT AND TRADEMARK OFFICE
CERTIFICATE OF CORRECTION

PATENT NO.    : 6,878,685 B2                                              Page 1 of 1
DATED         : April 12, 2005
INVENTOR(S)   : David R. Soll et al.

It is certified that error appears in the above-identified patent and that said Letters Patent is hereby corrected as shown below:

<u>Column 1,</u>
Line 7, insert the following:
-- The invention disclosed herein was made with Government support under NIH Grant Nos. DE12161 and NIAID AI40040 from the National Institutes of Health. Accordingly, the U.S. Government has certain rights in this invention. --.

Signed and Sealed this

Thirteenth Day of September, 2005

JON W. DUDAS
*Director of the United States Patent and Trademark Office*